US00PP22291P2

(12) United States Plant Patent
Giesen

(10) Patent No.: US PP22,291 P2
(45) Date of Patent: Nov. 29, 2011

(54) ***LOBELIA* PLANT NAMED 'TEC TRAVIO'**

(50) Latin Name: *Lobelia erinus*
Varietal Denomination: Tec Travio

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/804,061

(22) Filed: Jul. 13, 2010

(51) Int. Cl.
*A01H 5/00* (2006.01)

(52) U.S. Cl. ..... Plt./451

(58) Field of Classification Search ..... Plt./451
See application file for complete search history.

*Primary Examiner* — June Hwu
*Assistant Examiner* — Louanne Krawczewicz Myers
(74) *Attorney, Agent, or Firm* — S. Matthew Edwards

(57) ABSTRACT

A new *Lobelia* plant named 'Tec Travio' particularly distinguished by the large intense purple-violet colored flowers, medium green foliage, vigorous, mounding, but semi-trailing and well branched habit with early flowering.

1 Drawing Sheet

Latin name of the genus and species of the plant claimed: *Lobelia erinus.*

Varietal denomination: 'Tec Travio'.

BACKGROUND OF THE NEW PLANT

The present invention comprises a new *Lobelia*, botanically known as *Lobelia erinus*, and hereinafter referred to by the variety name 'Tec Travio'.

'Tec Travio' is a product of a planned breeding program. The new cultivar has large intense purple-violet colored flowers, medium green foliage, vigorous, mounding but semi-trailing and well branched habit with early flowering.

'Tec Travio' originated from a hybridization made in a controlled breeding environment in Andijk, Netherlands. The female parent was the proprietary, unpatented plant designated 'LOB06-225-1' with pink flower color, smaller flower size, and lighter green leaves.

The male parent of 'Tec Travio' was an unpatented, proprietary plant designated as 'LOB02-14-1' with blue flower color, lighter green leaves, larger flower size and is less trailing in habit. The resultant seed was sown in September 2006.

'Tec Travio' was selected as one flowering plant within the progeny of the stated cross in December 2006 in a controlled environment in Andijk, Netherlands.

The first act of asexual reproduction of 'Tec Travio' was accomplished when vegetative cuttings were propagated from the initial selection in December 2006 in a controlled environment in Andijk, Netherlands.

BRIEF SUMMARY OF INVENTION

Horticultural examination of plants grown from cuttings of the plant initiated in December 2006, and continuing thereafter, has demonstrated that the combination of characteristics as herein disclosed for 'Tec Travio' are firmly fixed and are retained through successive generations of asexual reproduction.

'Tec Travio' has not been observed under all possible environmental conditions. The phenotype may vary significantly with variations in environment such as temperature, light intensity and day length.

Plant Breeder's Rights for this cultivar were applied for in Canada on Feb. 18, 2010 (#10-6849), in CVPO on Feb. 5, 2010 (#2010/0547), and in Switzerland on Oct. 29, 2009 (#09-2618). 'Tec Travio' has not been made publicly available more than one year prior to the filing of this application.

The following traits have been repeatedly observed and are determined to be basic characteristics of the new variety. The combination of these characteristics distinguishes this *Lobelia* as a new and distinct variety.

BRIEF DESCRIPTION OF THE PHOTOGRAPHS

The accompanying photographic drawing shows typical flower and foliage characteristics of 'Tec Travio' with colors being as true as possible with an illustration of this type.

The photographic drawing shows three flowering potted plants growing in one container of the new variety and a close-up of the flowers.

DETAILED BOTANICAL DESCRIPTION

The plant descriptions, measurements and aforementioned photographs were taken in Gilroy, Calif. from plants growing in an 8 inch basket in a greenhouse trial in April 2010. These plants were approximately 13-14 weeks of age.

Color references are made to The Royal Horticultural Society Colour Chart (R.H.S.) 2001.

TABLE 1

DIFFERENCES BETWEEN THE NEW VARIETY 'TEC TRAVIO' AND A SIMILAR VARIETY

| | 'Tec Travio' | 'Lobmounlila' (U. S . Plant Pat. No. 18,410) |
|---|---|---|
| Plant habit: | More trailing | Less trailing |
| Flower size: | Larger | Smaller |
| Stem diameter: | Larger | Smaller |
| Foliage color: | Darker green | Lighter green |

Plant:

*Form, growth and habit.*—Vigorous growth habit, dense and freely branched with medium long internodes, initially low spreading becoming more trailing.

*Plant height.*—About 20 cm.
*Plant height (inflorescence included).*—About 30 cm.
*Plant width.*—About 30 cm.
*Garden performance and tolerance to weather.*—Good.
*Crop time to flowering.*—About 10 weeks.

Roots:
*Number of days to initiate roots and develop roots.*—21-24 days at about 22 degrees C.
*Type.*—Fine, fibrous, free branching.
*Color.*—RHS N155B but whiter.

Foliage:
*Arrangement.*—Alternate.
*Immature, leaf color, upper surface.*—Closest to RHS 144A with a few darker patches.
*Lower surface.*—Closest to RHS 144B.
*Mature, leaf color, upper surface.*—Closest to RHS 137A but a little lighter.
*Lower surface.*—RHS 138A.
*Length.*—4.5-6.5 cm.
*Width.*—1.4-1.7 cm.
*Shape.*—Oblong.
*Base shape.*—Fused.
*Apex shape.*—Praemorse.
*Margin.*—Serrate.
*Texture, upper surface.*—Slightly hirsute; hispid.
*Lower surface.*—Slightly hirsute; hispid.
*Color of veins, upper surface.*—Indistinct.
*Color of veins, lower surface.*—Indistinct.

Stem:
*Quantity of main branches per plant.*—10-15.
*Color of stem.*—Between RHS 144A and RHS 144B.
*Length of stem.*—About 40 cm.
*Diameter.*—0.2-0.3 cm.
*Length of internodes.*—1.5-3.0 cm.
*Texture.*—Sparsely hirsute.

Inflorescence:
*Type.*—Raceme, terminal (at stem end), composed of single flowers in an alternate arrangement, with one flower per node, subtended by a narrow leaflet.
*Blooming habit.*—Continuous through the growing season.
*Quantity of flowers per plant.*—About 50, and numerous buds.
*Quantity of flowers per peduncle.*—3-4 open, with numerous buds.
*Lastingness of individual blooms on the plant.*—5-7 days depending on temperature.
*Fragrance.*—None.
*Color of peduncle.*—RHS 137A.
*Length of peduncle.*—5.0-5.5 cm.
*Peduncle diameter.*—0.1 cm.
*Peduncle texture.*—Slightly hirsute.
*Color of pedicels.*—RHS 137A.
*Length of pedicels.*—2-2.3 cm.
*Diameter of pedicels.*—0.075 cm.
*Pedicel texture.*—Slightly hirsute.

Bud (just when starting to show color):
*Color.*—RHS 147D; RHS N77B but a little lighter at the apex.
*Length.*—1.0-1.2 cm.
*Width.*—0.4 cm.
*Shape.*—Oblong.

Flower:
*Corolla type.*—Single, zygomorphic; upper lip has two small lobes and lower lip has three larger and broader lobes; lobes are fused at the base.

Immature inflorescence:
*Flower diameter.*—1.8-2.1 cm.
*Flower color, upper surface.*—Closest to RHS N81A.
*Lower surface.*—Closest to RHS 77B.

Mature inflorescence:
*Flower depth.*—2.2 cm.
*Flower length.*—2.3-2.5 cm.
*Color upper petals, upper surface.*—Between RHS N81A and RHS N80A.
*Lower surface.*—RHS 77B with RHS 77A blotches.
*Upper petals, length (from the corolla opening).*—0.8 cm.
*Upper petals, width.*—0.3 cm.
*Color lower petals, upper surface.*—Between RHS N81A and RHS N80A with a spot of closest to RHS N79C basally on the mid vein; at the very base, a white blotch with a spot of RHS 3B.
*Lower surface.*—RHS 77B with RHS 77A blotches; and white basally.
*Lower petals, length (from the corolla opening).*—1.1-1.2 cm.
*Lower petals, width.*—0.7-0.8 cm.

Petal (all lobes):
*Petal shape.*—Obovate.
*Apex shape.*—Mucronulate.
*Base.*—Fused.
*Margin.*—Entire.
*Petal texture, upper surface.*—Smooth, glabrous, slightly Pubescent.
*Lower surface.*—Glabrous.
*Corolla tube color, outside.*—RHS N81B.
*Inside.*—RHS N155A with RHS N79C blotches and lines of RHS 1B.
*Corolla tube length.*—0.7-0.8 cm.
*Tube width.*—0.4 cm.
*Texture, inside.*—Hirsute.
*Outside.*—Papillose.

Calyx:
*Quantity and form.*—5 sepals in a whorl, fused at the base and somewhat funnel shaped.
*Color, upper surface.*—RHS 147A but a little lighter.
*Lower surface.*—RHS 147A but a little lighter.
*Length.*—0.8-0.9 cm.
*Width.*—0.15 cm.
*Shape.*—Ligulate.
*Apex shape.*—Acute.
*Base.*—Fused.
*Margins.*—Entire.
*Texture, upper surface.*—Glossy and glabrous.
*Lower surface.*—Hirsute.

Reproductive organs:
*Pistil.*—1.
*Length.*—0.8-0.9 cm.
*Style color.*—RHS 144A.
*Style length.*—0.6-0.7 cm.
*Stigma color.*—RHS 59B.
*Ovary color.*—RHS 145C.
*Ovary length.*—0.2-0.3 cm.
*Ovary width.*—0.1-0.15 cm.
*Stamens.*—5.

*Color of filaments.*—RHS 72A at the anthers and white basally.
*Length filaments.*—0.7 cm.
*Anther color.*—RHS N187A.
*Anther length.*—0.2-0.3 cm.
*Color of pollen.*—RHS 4D.
*Pollen amount.*—Abundant.
*Fertility/seed set.*—Has not been observed on this hybrid.

Disease/pest resistance: Disease/pest resistance has not been observed on this hybrid.

What is claimed is:

1. A new and distinct variety of *Lobelia* plant named 'Tec Travio' substantially as illustrated and described herein.

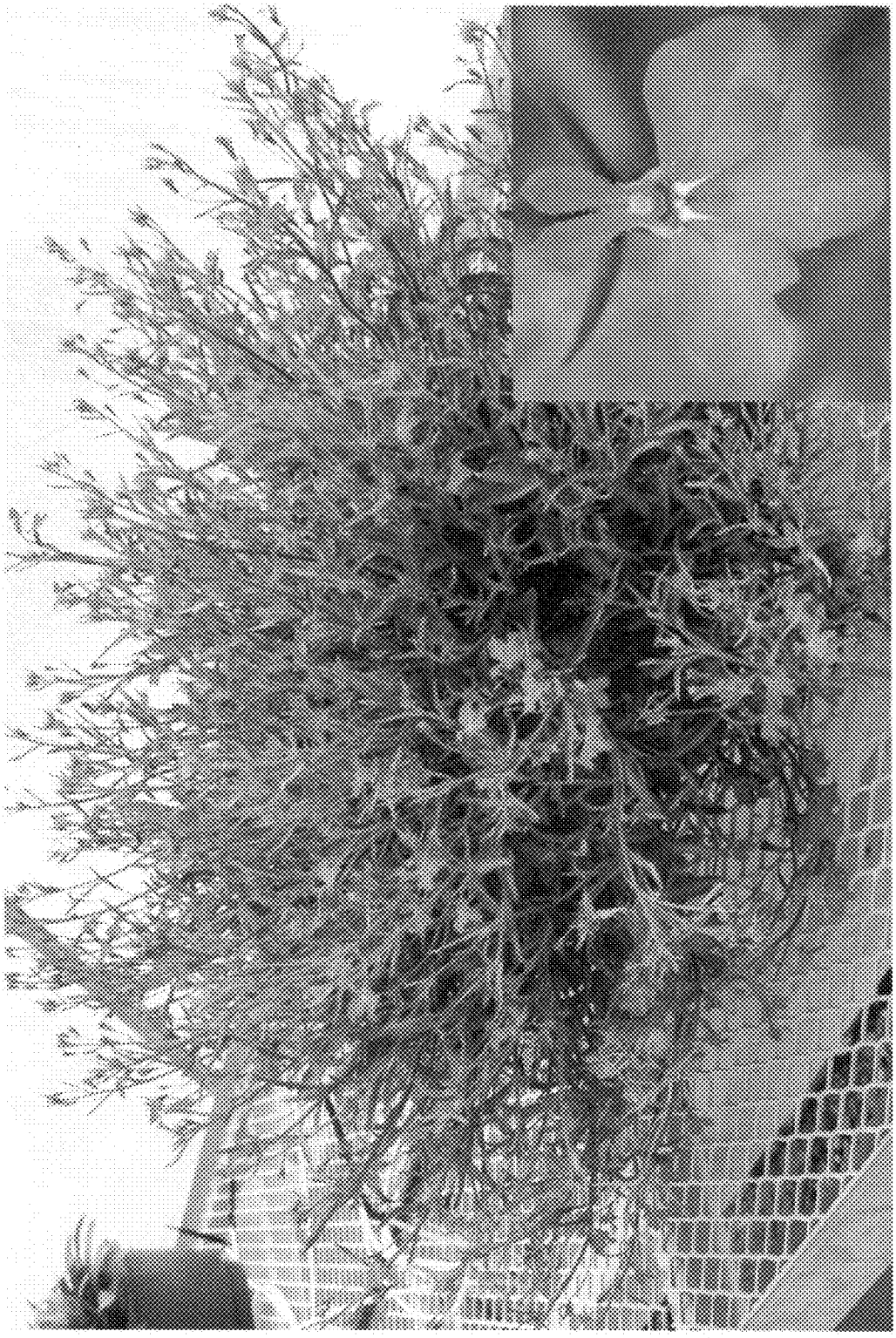

* * * * *